US011554096B2

(12) United States Patent
Yoo et al.

(10) Patent No.: US 11,554,096 B2
(45) Date of Patent: Jan. 17, 2023

(54) PROBIOTICS-DELIVERING HYDROGEL FORMULATION FOR PROTECTING PROBIOTICS IN ACIDIC ENVIRONMENT AND COMPOSITION FOR DELIVERING PROBIOTICS COMPRISING SAME

(71) Applicant: PUSAN NATIONAL UNIVERSITY INDUSTRY-UNIVERSITY COOPERATION FOUNDATION, Busan (KR)

(72) Inventors: Jin-Wook Yoo, Busan (KR); Ji Hyun Kim, Busan (KR)

(73) Assignee: PUSAN NATIONAL UNIVERSITY INDUSTRY-UNIVERSITY COOPERATION FOUNDATION, Busan (KR)

( * ) Notice: Subject to any disclaimer, the term of this patent is extended or adjusted under 35 U.S.C. 154(b) by 34 days.

(21) Appl. No.: 16/622,286

(22) PCT Filed: Jun. 12, 2018

(86) PCT No.: PCT/KR2018/006652
§ 371 (c)(1),
(2) Date: Dec. 12, 2019

(87) PCT Pub. No.: WO2018/230939
PCT Pub. Date: Dec. 20, 2018

(65) Prior Publication Data
US 2020/0197301 A1 Jun. 25, 2020

(30) Foreign Application Priority Data

Jun. 13, 2017 (KR) .................. 10-2017-0074383
Mar. 12, 2018 (KR) .................. 10-2018-0028686

(51) Int. Cl.
| | |
|---|---|
| *A61K 9/06* | (2006.01) |
| *A61K 35/741* | (2015.01) |
| *A23L 33/135* | (2016.01) |
| *A61K 47/42* | (2017.01) |
| *A61K 47/38* | (2006.01) |

(52) U.S. Cl.
CPC ............ *A61K 9/06* (2013.01); *A23L 33/135* (2016.08); *A61K 35/741* (2013.01); *A61K 47/38* (2013.01); *A61K 47/42* (2013.01)

(58) Field of Classification Search
CPC ........ A61K 9/06; A61K 35/741; A61K 47/42; A61K 47/38; A23L 33/135
See application file for complete search history.

(56) References Cited

U.S. PATENT DOCUMENTS

| | | | | |
|---|---|---|---|---|
| 2009/0238890 | A1* | 9/2009 | Piechocki | ............... C08J 3/122 |
| | | | | 424/501 |
| 2011/0217368 | A1* | 9/2011 | Prakash | .................. A61P 9/10 |
| | | | | 424/451 |
| 2012/0135017 | A1* | 5/2012 | Harel | ................... A23L 29/06 |
| | | | | 424/184.1 |
| 2014/0010918 | A1 | 1/2014 | Quintens et al. | |
| 2018/0070586 | A1* | 3/2018 | Kim | ..................... A01N 25/22 |

FOREIGN PATENT DOCUMENTS

| | | | |
|---|---|---|---|
| JP | 5950938 | B2 | 7/2016 |
| KR | 10-2000-0043838 | A | 7/2000 |
| KR | 10-2002-0063978 | A | 8/2002 |
| KR | 10-2009-0076438 | * | 7/2009 |
| KR | 10-2009-0076438 | A | 7/2009 |
| KR | 10-1000952 | B1 | 12/2010 |
| KR | 101000952 | B1 * | 12/2010 |
| KR | 10-1487446 | B1 | 1/2015 |
| WO | 2012-150269 | A1 | 11/2012 |

OTHER PUBLICATIONS

Sami I. Somo, Omaditya Khanna, and Eric M. Brey, Alginate Microbeads for Cell and Protein Delivery in Cell Microencapsulation: Methods and Protocols, Methods in Molecular Biology, vol. 1479 p. 217-224 (available online Oct. 14, 2016 at https://link.springer.com/protocol/10.1007/978-1-4939-6364-5_17 (Year: 2016).*
International Search Report for PCT/KR2018/006652 dated Oct. 11, 2018 from Korean Intellectual Property Office.
Mathews, Smitha, "Microencapsulation of Probiotics by Calcium Alginate and Gelatin and Evaluation of its Survival in Simulated Human Gastro-Intestinal Condition", International Journal of Current Microbiology and Applied Sciences, Apr. 2017, vol. 6, No. 4, pp. 2080-2087.
Amal Bakr Shori, "Microencapsulation Improved Probiotics Survival During Gastric Transit", HAYATI Journal of Biosciences 24, 2017, pp. 1-5.
Omaditya Khanna et al., "Generation of Alginate Microspheres for Biomedical Applications", IJournal of Visualized Experiments, Aug. 2012, 66, e3388, pp. 1-5.
E Selmer-Olsen et al., "Survival of Lactobacillus helveticus entrapped in Ca-alginate in relation to water content, storage and rehydration", Journal of Industrial Microbiology & Biotechnology (1999) 23, 79-85.

* cited by examiner

*Primary Examiner* — Sean M Basquill
(74) *Attorney, Agent, or Firm* — Revolution IP, PLLC

(57) ABSTRACT

The present invention relates to a hydrogel formulation for delivering probiotics including a hydrogel, probiotics and zwitterionic buffer as an active ingredient, a composition for delivering probiotics comprising the same and a method of preparing the same, which adjust and maintain the internal pH of the hydrogel even in the gastric juice environment, thereby increasing the survival rate of the probiotics in the gastric juice and improving the delivery rate to the large intestine, by further adding zwitterionic buffer capable of maintaining pH to the hydrogel encapsulated with probiotics.

5 Claims, 8 Drawing Sheets

[FIG. 1]
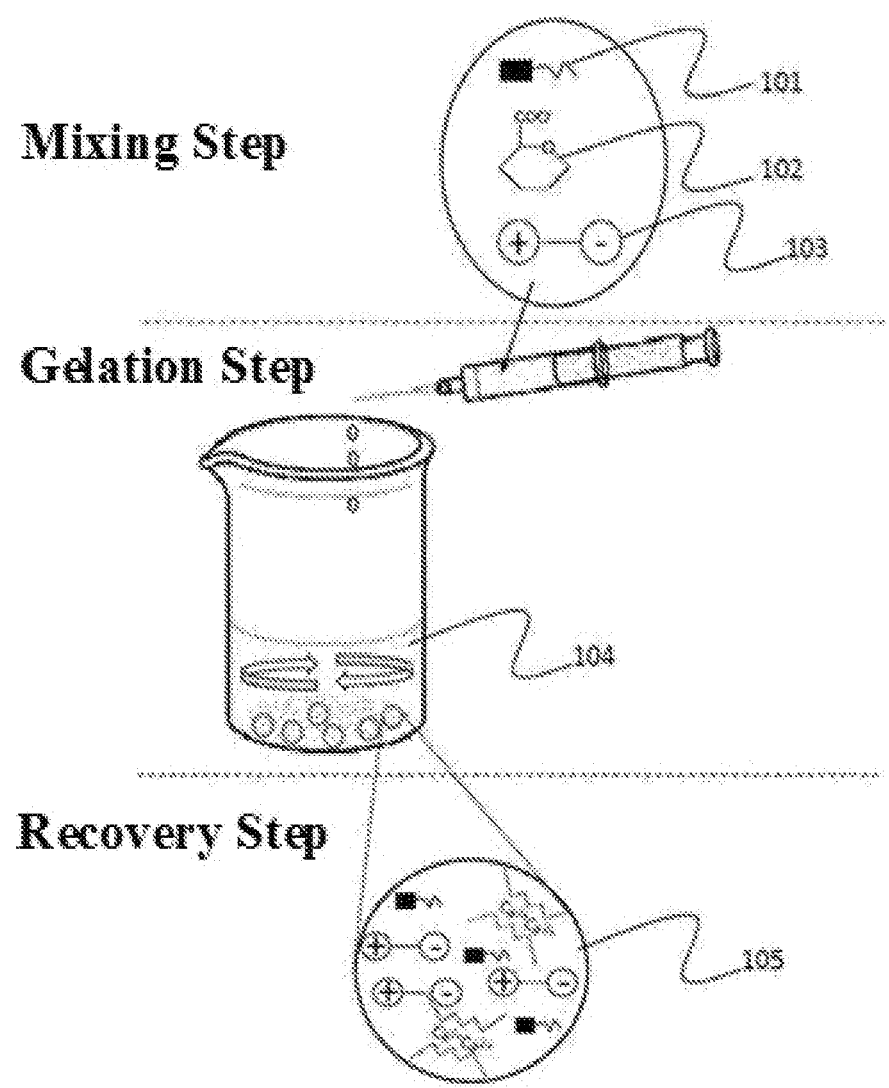

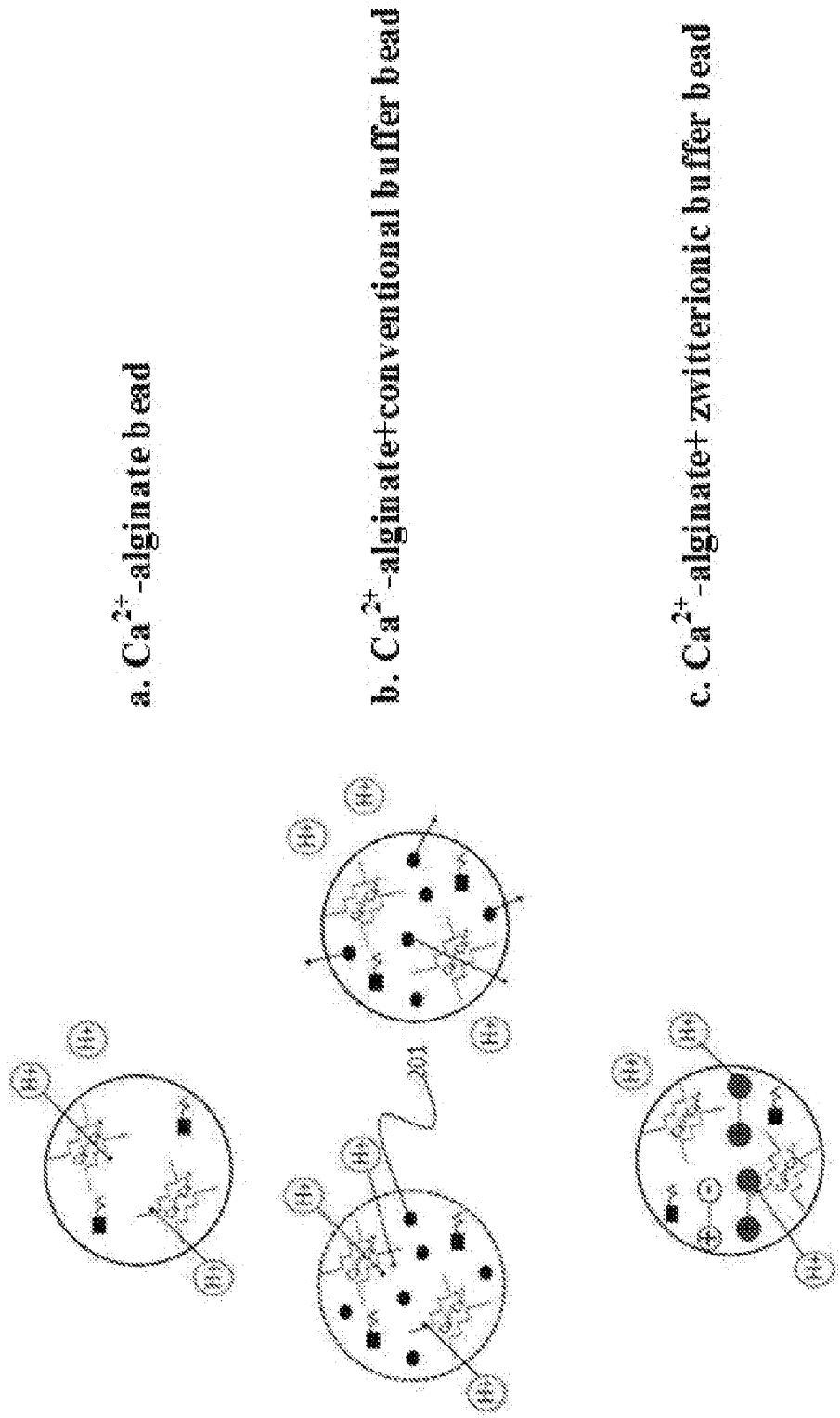
[FIG. 2]

[FIG. 3]
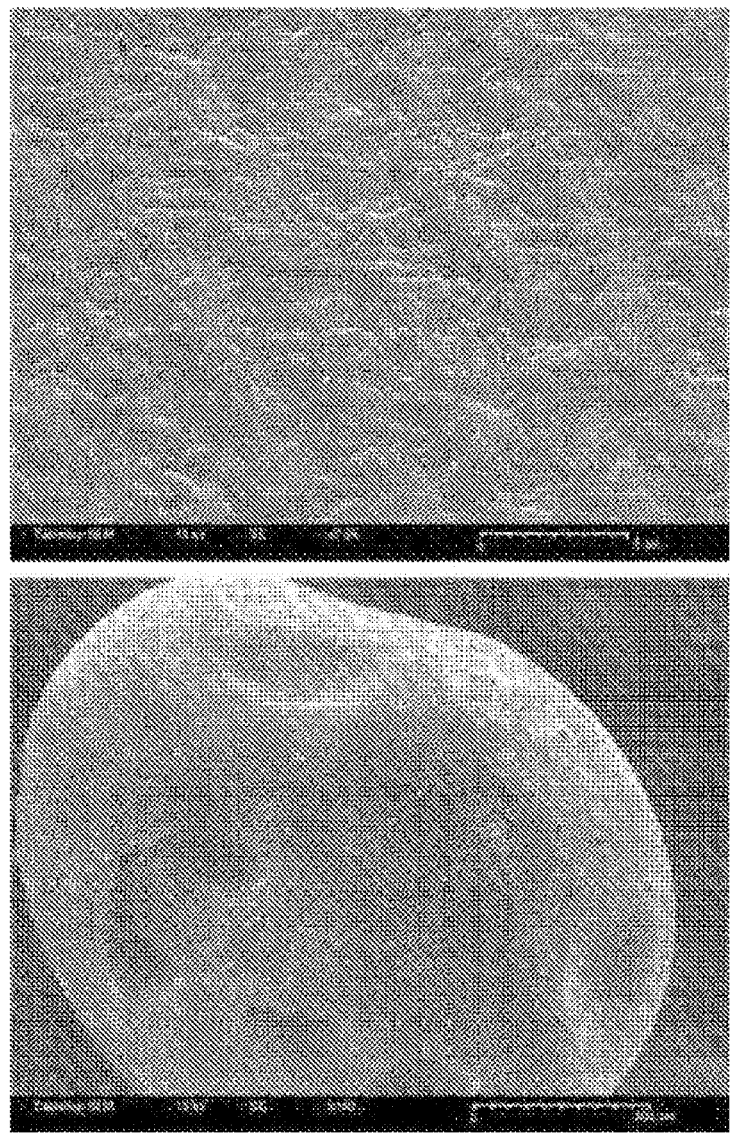

[FIG. 4]
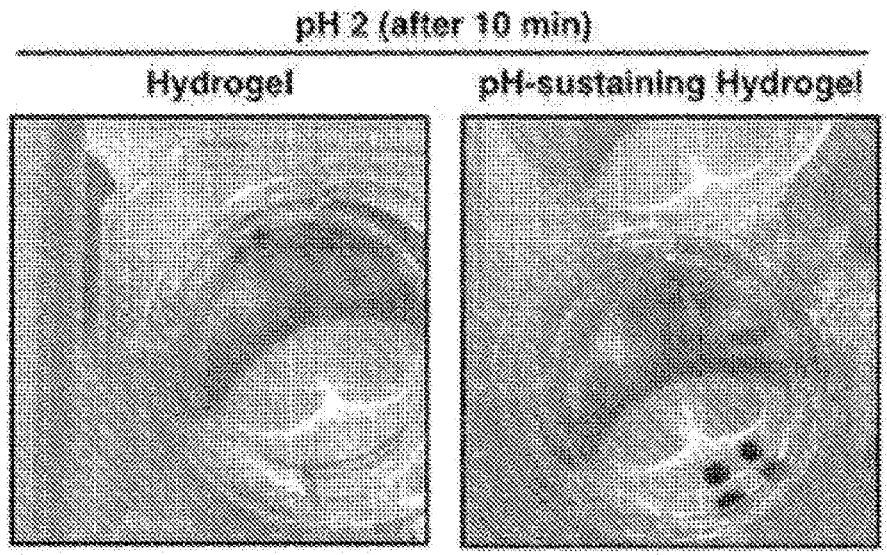
[FIG. 5]
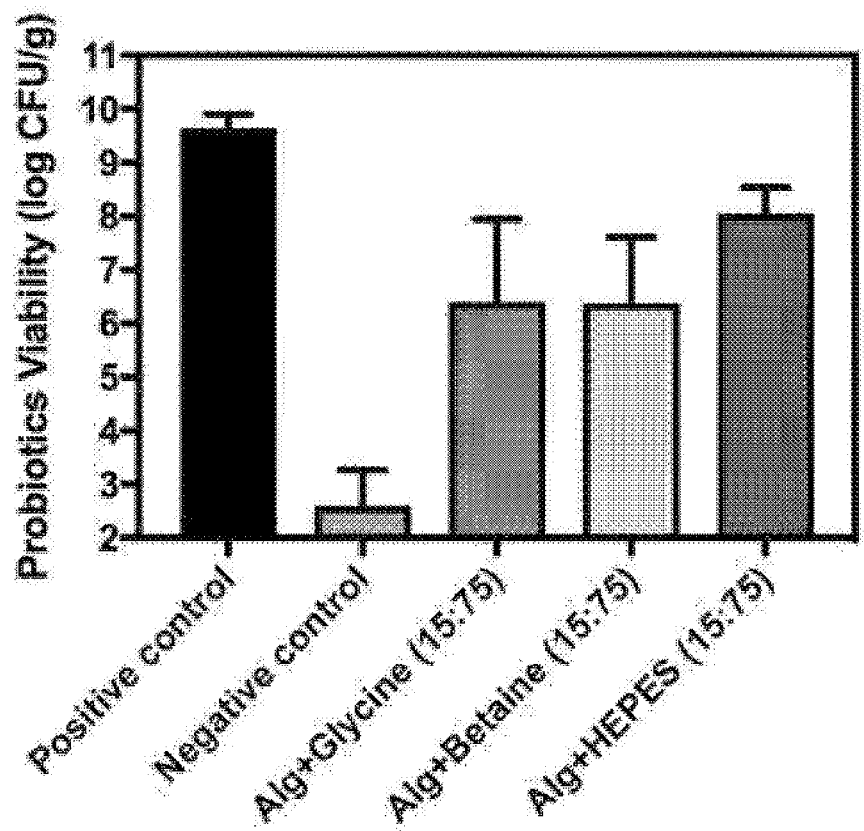

[FIG. 6]
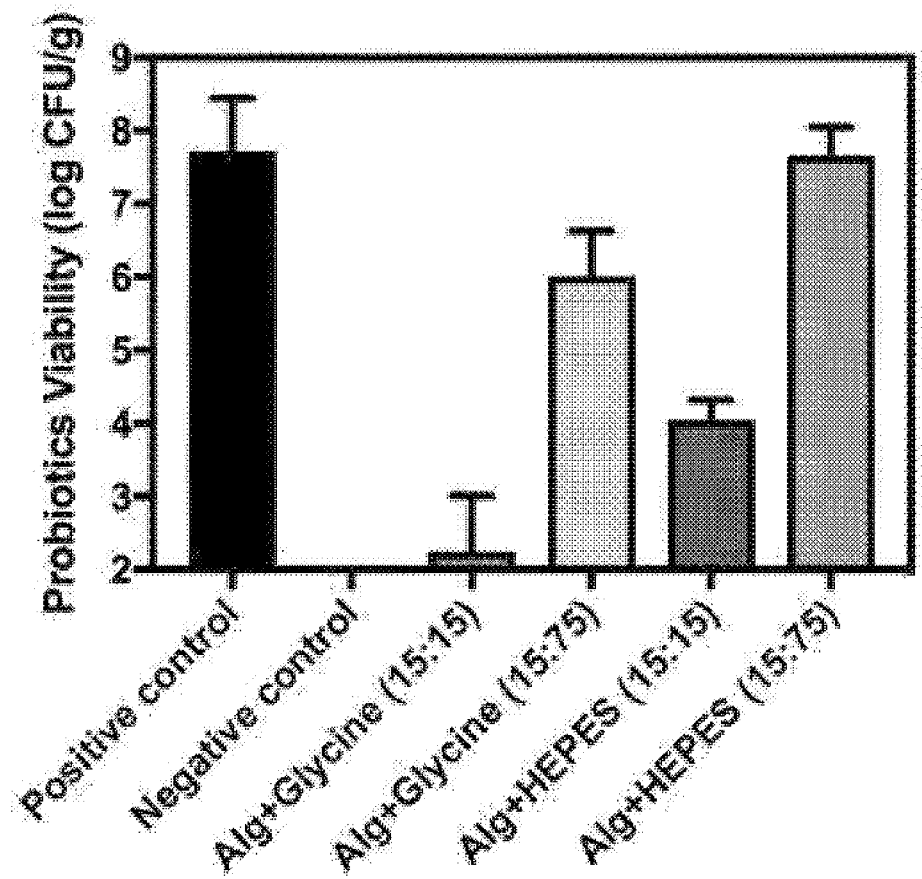

[FIG. 7]
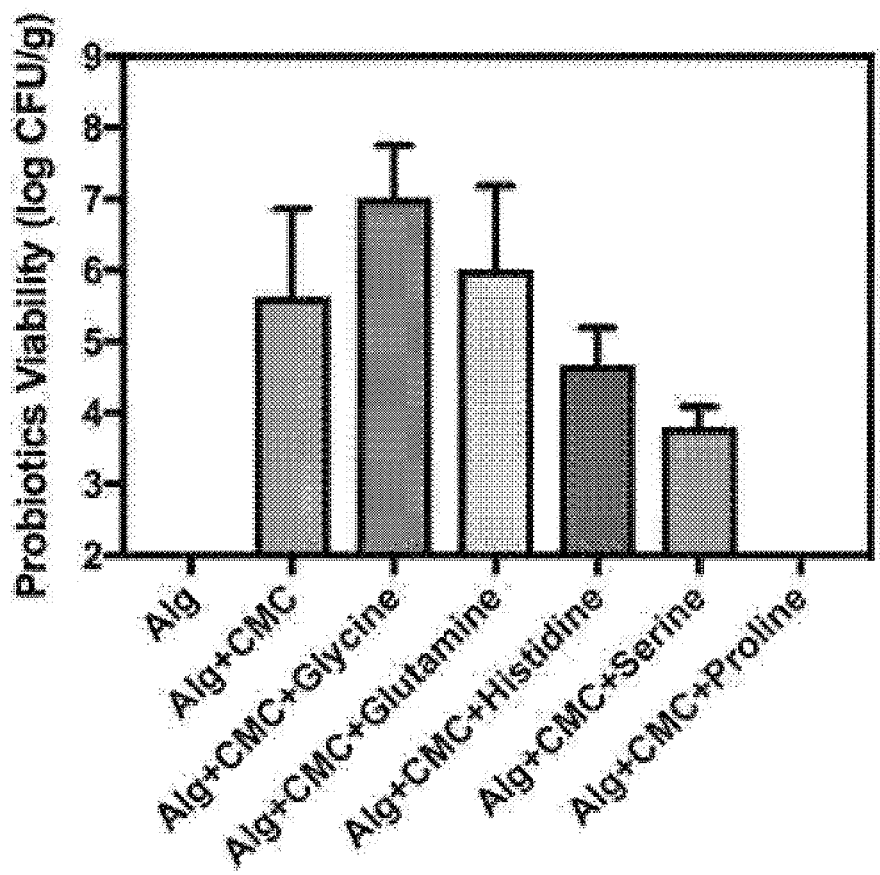

[FIG. 8]
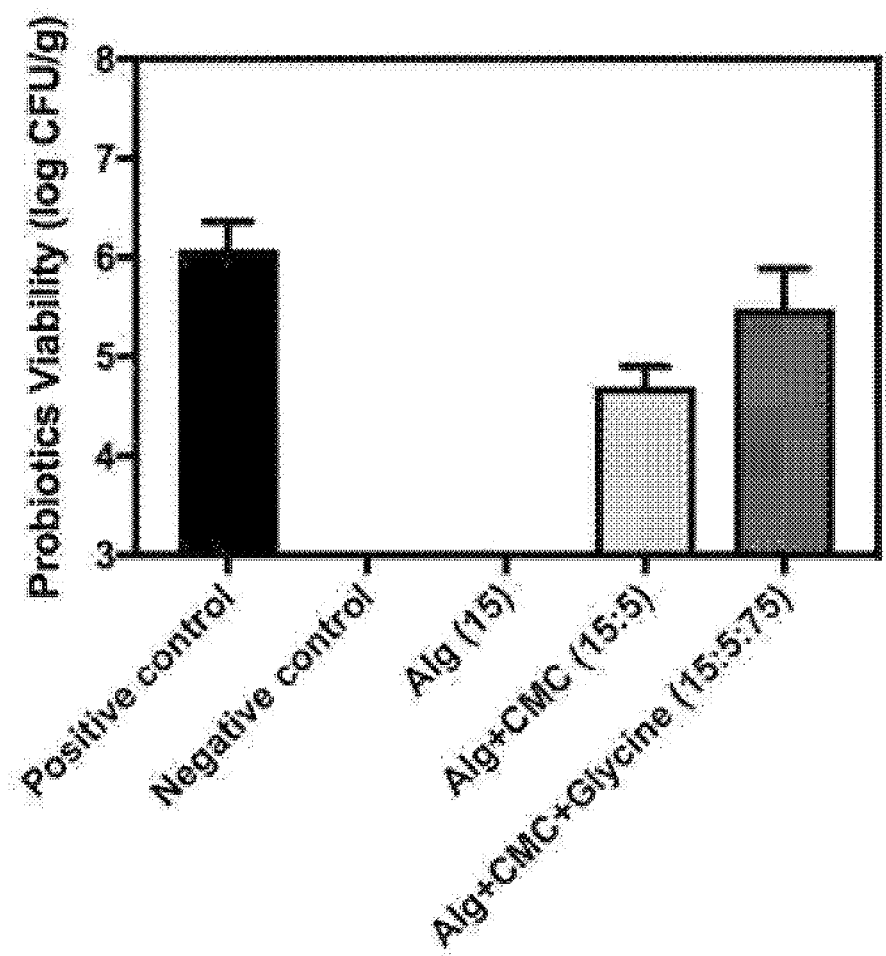

[FIG. 9]
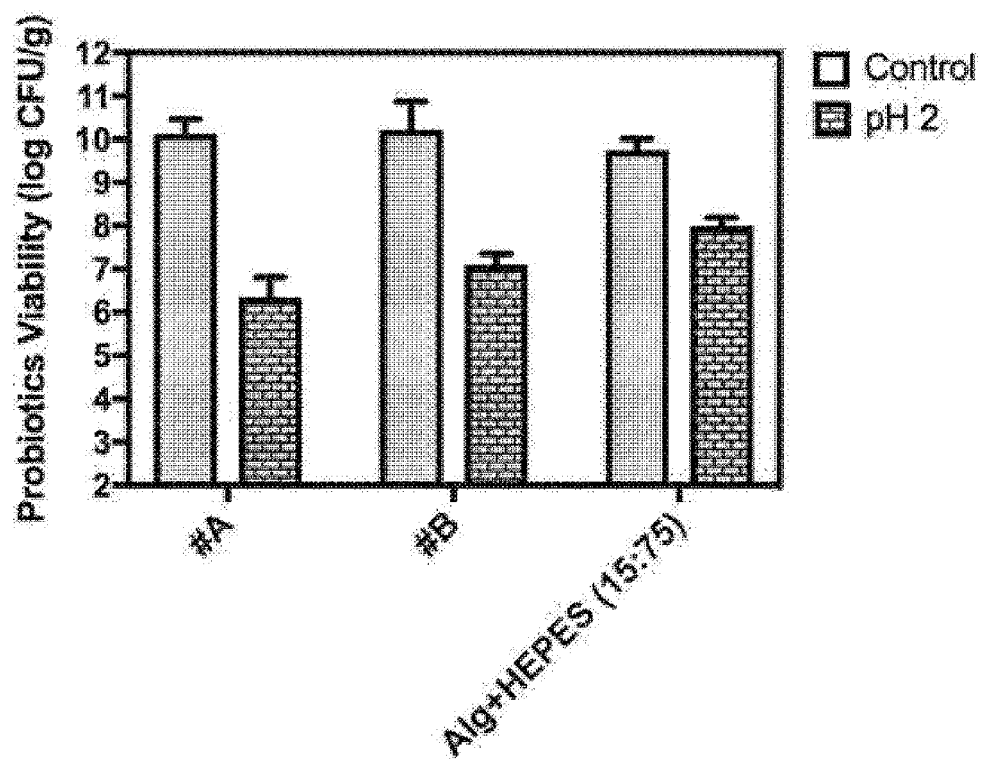

PROBIOTICS-DELIVERING HYDROGEL FORMULATION FOR PROTECTING PROBIOTICS IN ACIDIC ENVIRONMENT AND COMPOSITION FOR DELIVERING PROBIOTICS COMPRISING SAME

CROSS REFERENCE TO PRIOR APPLICATIONS

This application is a National Stage Application of PCT International Patent Application No. PCT/KR2018/006652 filed on Jun. 12, 2018, under 35 U.S.C. § 371, which claims priority to Korean Patent Application Nos. 10-2018-0028686 and 10-2017-0074383 filed on Mar. 12, 2018 and Jun. 13, 2017, respectively, which are all hereby incorporated by reference in their entirety.

TECHNICAL FIELD

The present invention relates to a hydrogel formulation for delivering probiotics comprising a hydrogel, probiotics and zwitterionic buffer as an active ingredient, a composition for delivering probiotics comprising the same and a method of preparing the same.

BACKGROUND ART

Probiotics are live bacteria and bacteria that help health by being taken in reasonable amount (FAO/WHO, 2012). In general, probiotics function in a living state in the intestine, and are effective for various diseases such as IBD, diarrhea, obesity and cancer as well as health promotion by control of intestinal immune function. To this end, the survival rate of probiotics must be ensured at all stages of production, storage and ingestion. In particular, probiotics after ingestion should not die by the gastric acid in a stomach and a sufficient amount of live bacteria must reach in an intestine. To this end, methods of taking a greater number of probiotics or encapsulating them in a probiotics delivery system are under discussion and research and development. Currently, the product containing the largest number of probiotics, i.e. $4.3 \times 10^{11}$ CFU/sachet contains about 10 times as many live bacteria than the general probiotics, but there is a limit in terms of price. In addition, although various delivery systems have been discussed, there are difficulties such as insufficient protection effect or no release at the target location (a), complex processes (b) or reduced viable count and functional loss in the encapsulation process.

In the case of probiotics delivery systems, the use of high temperatures, shear forces, pressures, osmotic pressure and organic solvents during the entire production process from incubation to ingestion, may result in reduced viable count and function. In addition, the additional processes for providing additional protection effect not only increases the cost burden, but also generates functional loss by prolonging the exposure time of the anaerobic probiotics to the external environment and reacting the added carrier material with the probiotics.

As such, probiotics delivery system should be made from materials that have been proven to be biologically stable in as simple process as possible. Through this, there is a difficulty in research and development and mass production in that the delivery system itself does not react with the probiotics, and the probiotics must be protected in various stress environments and also they must be completely released from the small and large intestine. In addition, because probiotics have a physiological activity and adaptation mechanism to external stress environments, factors that can impair these functions in the production process should be minimized.

DISCLOSURE

Technical Problem

It is an object of the present invention to provide a hydrogel formulation for delivering probiotics which can increase the delivery rate to the intestine by increasing the survival rate of probiotics in the stomach at low pH.

It is another object of the present invention to provide a pharmaceutical composition for delivering probiotics which can increase the delivery rate to the intestine by increasing the survival rate of probiotics in the stomach at low pH. It is the third object of the present invention is to provide a health food composition for delivering probiotics which can increase the delivery rate to the intestine by increasing the survival rate of probiotics in the stomach at low pH.

It is the fourth object of the present invention is to provide a method of preparing a hydrogel formulation for delivering probiotics which can increase the delivery rate to the intestine by increasing the survival rate of probiotics in the stomach at low pH.

Technical Solution

In order to achieve the above object, the present invention provides a hydrogel formulation for delivering probiotics comprising a hydrogel, probiotics and zwitterionic buffer as an active ingredient.

In order to achieve the above another object, the present invention provides a pharmaceutical composition for delivering probiotics comprising the hydrogel formulation as an active ingredient.

In order to achieve the above another object, the present invention provides a health functional food composition for delivering probiotics comprising the hydrogel formulation as an active ingredient.

In order to achieve the above another object, the present invention provides a method of preparing a hydrogel formulation for delivering probiotics comprising: (1) preparing a mixed solution by adding probiotics and zwitterionic buffer to hydrogel solution; and (2) encapsulating the probiotics and the zwitterionic buffer in the hydrogel by dropping the mixed solution into a solution of calcium chloride ($CaCl_2$).

Advantageous Effects

A hydrogel formulation for delivering probiotics and a composition comprising the same according to the present invention have a short external exposure time of the bacteria, no reaction between the substances added for giving the capability of pH control and the bacteria and physical blocking of $H^+$ ions and further maintenance of a proper pH by actively neutralizing $H^+$ ions introduced into the inside and therefore they can effectively improve the delivery rate of the probiotics to the intestine, and their production methods also has the advantage of easy mass production because they consist of simple methods of bacteria harvest after culture, mixing and gelling.

DESCRIPTION OF DRAWINGS

FIG. 1 schematically shows a process of preparing a hydrogel formulation encapsulating probiotics according to an embodiment of the present invention.

FIG. 2 schematically shows the difference between a hydrogel formulation according to an embodiment of the present invention and the conventional hydrogel formulation and the mode of action.

FIG. 3 shows SEM images of probiotics and a hydrogel composition encapsulating probiotics of an embodiment of the present invention.

FIG. 4 shows a result of observing the change in the internal pH of the hydrogel common in artificial gastric juice and a hydrogel prepared in the present invention.

FIG. 5 shows a result of confirming the effect on the acid resistance when the probiotics are included in the alginate containing zwitterionic buffer in a formulation according to the present invention.

FIG. 6 shows a result of confirming the acid resistance effect according to the content of the zwitterionic buffer in a formulation of the present invention.

FIG. 7 shows a result of confirming the acid resistance effect according to each amino acid in case of using different types of amino acids in a formulation according to the present invention.

FIG. 8 shows a result of confirming the acid resistance effect after the freeze-drying process of a formulation according to the present invention.

FIG. 9 shows a result of comparing the acid resistance effects of commercialized products and a formulation according to the present invention.

BEST MODE

In the present invention, a pH-sustaining hydrogel system was added to a previously developed hydrogel-based delivery system in one step, and used for the delivery of probiotics. Because probiotics die by low pH or enzymes present in the body, a protective effect for them is essential. The present invention confirmed that the composition for delivering probiotics prepared in one embodiment of the present invention has a proper pH even if $H^+$ ions introduced from the upper digestive tract are introduced into its inside and confirming that exhibits activity even after the exposure of the probiotics to artificial gastric juice for 2 hours and the present invention was completed.

Accordingly, the present invention provides a hydrogel formulation for delivering probiotics comprising a hydrogel, probiotics and zwitterionic buffer as an active ingredient.

As disclosed in FIG. 1 of the present invention, probiotics 101 and zwitterionic buffer 103 are mixed in an alginate solution (1.0-3.0%, 102) which is one of the hydrogels, and then placed in a syringe and added dropwise into a beaker containing $CaCl_2$ (0.05-0.25 M; 104) solution to obtain a hydrogel formulation 105 encapsulating both probiotics and zwitterionic buffer. Because L-gluronic acid (G) residue of the alginate reacts with $Ca^{2+}$ ions to undergo gelation in the form of an egg box and D-mannuronic acid (M) residue does not participate in gelation, carboxyl group (—COOH) that can react remains. The remaining carboxyl groups are involved in shrinking or swelling the alginate network structure according to pH.

Namely, pKa of the alginate is about 3.2, and at pH 2.0 it is generally present in the form of COOH to be dense, and at pH 6.8 and above it becomes COO—, resulting in electrical repulsion and loosening. Using this property, $Ca^{2+}$-alginates have been used in drug delivery platforms targeting the intestine in the past. Conventionally, alginate gels for probiotics were generally coated with chitosan, since it is known that a semi-interpenetrating polymer network (IPN) is formed with a negatively charged alginate because the amino group of chitosan has a (+) charge at pH 2 to slow down the penetration of hydrogen ions from stomach acids.

Thus, in the present invention, zwitterionic buffers were mixed in Ca-alginate formulation gels to neutralize hydrogen ions entering the pores of alginate. At this time, as shown in FIG. 2, when only the Ca-alginate gel was used (FIG. 2(a)), the pores of the Ca-alginate are at least 5 nm so that hydrogen ions are introduced through them, thus probiotics die in the stomach. Conversely, in the case of using the general buffer 201, as shown in FIG. 2(b), the buffer damages the Ca-alginate structure to introduce hydrogen ions (left), or the buffers exit the formulation and hydrogen ions are introduced (right), causing probiotics to die.

However, in the formulation according to the present invention, as shown in FIG. 2(c), the zwitterionic buffer is present in the gel and at the same time neutralizes the hydrogen ions permeating into the gel to buffer the pH change in the gel. As a result, due to the excessive influx of hydrogen ions, metabolism, proteins, DNA, etc. are damaged, and the dying probiotics are neutralized with zwitterionic buffers to make them survive.

In detail, the hydrogel may be selected from the group consisting of alginate, pectin, carrageenan and gelatin, but it is not limited thereto.

The probiotics may be at least one selected from the group consisting of strains of *Lactobacillus* sp., *Streptococcus* sp., *Lactococcus* sp., *Enterococcus* sp., *Pediococcus* sp., *Leuconostock* sp., *Weissella* sp. and *Bifidobacterium* sp., but it is not limited thereto.

In more detail, the probiotics may be at least one selected from the group consisting of *Lactobacillus acidophilus*, *Lactobacillus casei*, *Lactobacilus gasseri*, *Lactobacillus delbrueckii* spp. *bulgaricus*, *Lactobacillus helveticus*, *Lactobacillus fermentum*, *Lactobacillus paracasei*, *Lactobacillus plantarum*, *Lactobacillus reuteri*, *Lactobacillus rhamnosus*, *Lactobacillus salivarius*, *Lactococcus lactis*, *Enterrococcus faecium*, *Enterococcus faecalis*, *Streptococcus thermophilus*, *Bifidobacterium bifidum*, *Bifidobacterium breve*, *Bifidobacterium longum* and *Bifidobacterium animalis* ssp. *lactis*, but it is not limited thereto.

At this time, the probiotics can be present in the form encapsulated in the hydrogel, and thus probiotics can be protected by the hydrogel to maximize the delivery rate to the intestine.

The zwitterionic buffers may be selected from the group consisting of N-(2-hydroxyethyl)-piperazine-1-N'-2-ethanesulfonic acid (HEPES), glycine and betaine and thus in particular, the zwitterionic buffer has an excellent acid resistance improving effect and is preferable.

In one embodiment of the present invention, it may include in amount of 0.5 to 5.0 parts by weight of the hydrogel, 0.1 to 10.0 parts by weight of the zwitterionic buffer and 0.00001 to 1 parts by weight of the probiotics, based on 100 parts by weight of the hydrogel formulation, and if it exceeds this content range or is included below the content range, the absolute amount of probiotics delivered to the intestine is insufficient or the stability of the formulation is degraded so that probiotics cannot be delivered safely to the intestine, and it is not preferable.

In this case, the probiotics may be included in 7 to 12 log CFU/g.

In addition, in the hydrogel formulation, alginate is present in the form that alginate catches water, zwitterionic buffers and probiotics and thus it may further contain 80 parts by weight to 99.5 parts by weight of water relative to 100 parts by weight of the hydrogel formulation. However, the weight of water may be converged to zero by drying.

The weight ratio of the hydrogel and zwitterionic buffer may be 1:5 to 5:1, and particularly, the weight ratio of the hydrogel and zwitterionic buffer may be 1:5 to 1:1, and more particularly, the weight ratio of the hydrogel and the zwitterionic buffer may be 1:5, and when included in the above ratio, it is preferable because the delivery rate of the probiotics to the intestine is maximized, wherein the probiotics of 7 to 12 log CFU/g may be included.

In one embodiment of the present invention, the formulation may further comprise carboxymethylcellulose, and in particular, it includes glycine as a zwitterionic buffer which is preferred because it can maximize the pH neutralizing effect.

In addition, the formulation may be freeze-dried or low temperature vacuum-dried, and when the formulation is freeze-dried, it is preferable because the acid resistance properties are further improved, even if it undergoes a process for the commercialization, the effect of delivering probiotics to the intestine may be maintained or maximized.

In one embodiment of the present invention, the formulation may be in a regular form or an amorphous form having an average diameter of 200 to 3000 and may be in the form of a gel including water, but it is not limited thereto.

In addition, during the drying process, it may be in may be in a regular form or an amorphous form having an average diameter of 40 to 700 but it is not limited thereto.

More specifically, the hydrogel formulation may be, for example, in the form of beads, but it is not limited thereto.

In this case, the zwitterionic buffer may improve acid resistance of the formulation by neutralizing hydrogen ions entering the formulation to deliver probiotics to the intestine.

In addition, the present invention provides a pharmaceutical composition for delivering probiotics comprising the hydrogel formulation as an active ingredient.

The hydrogel formulation may be included in an amount of 0.01 to 90 parts by weight based on 100 parts by weight of the pharmaceutical composition, but it is not limited thereto.

The pharmaceutical composition according to the present invention may further comprise a suitable carrier, excipient or diluent commonly used in the preparation of the pharmaceutical composition in addition to the hydrogel formulation. Carriers, excipients or diluents which can be used in the present invention include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methylhydroxybenzoate, propyl hydroxybenzoate, talc, magnesium stearate, mineral oil and the like.

In one embodiment of the present invention, the pharmaceutical composition may be any one formulation selected from the group consisting of eye drops, granules, tablets, pills, capsules, gels, syrups, suspensions, emulsions, drops, solutions and injections, but it is not limited thereto.

When formulated, it is prepared by using diluents or excipients such as fillers, bulking agents, binders, wetting agents, disintegrating agents and surfactants which are commonly used. Solid preparations for oral administration include tablets, pills, powders, granules, capsules and the like, and such solid preparations may be prepared by mixing at least one excipient such as starch, calcium carbonate, sucrose, lactose, gelatin, etc.

Further, in addition to simple excipients, lubricants such as magnesium stearate, talc are also used. Oral liquid preparations include suspensions, oral solutions, emulsions, and syrups, and may include various excipients such as wetting agents, sweeteners, fragrances, preservatives and the like in addition to commonly used simple diluents such as water and liquid paraffin.

Formulations for parenteral administration include sterile aqueous solutions, non-aqueous solvents, suspensions, emulsions, freeze drying agents, suppositories. As the non-aqueous solvents and suspensions, propylene glycol, polyethylene glycol, vegetable oils such as olive oil, injectable esters such as ethyl oleate, and the like may be used. As the base of the suppository, witepsol, macrogol, tween 61, cacao butter, laurinum, glycerogelatin and the like may be used.

In addition, the dosage of the pharmaceutical composition according to the present invention may be increased or decreased depending on the route of administration, the severity of the disease, sex, weight, age, and the like. Therefore, the above dosage does not limit the scope of the present invention in any aspect.

The present invention also provides a health functional food composition for delivering probiotics comprising the hydrogel formulation as an active ingredient.

The hydrogel formulation may be included in an amount of 0.01 to 80 parts by weight based on 100 parts by weight of the health functional food composition, but it is not limited thereto.

The health functional food composition includes various nutrients, vitamins, minerals (electrolytes), flavors such as synthetic flavors and natural flavors, colorants and fillers (cheese, chocolate, etc.), pectic acid and salts thereof, alginic acid and salts thereof, organic acids, protective colloid thickeners, pH adjusting agents, stabilizers, preservatives, glycerin, alcohols, carbonating agents used in carbonated drinks, and the like. Besides, it may contain flesh for the preparation of natural fruit juices, synthetic fruit juices and vegetable drinks. These components may be used independently or in combination. In addition, the health functional food composition may be in the form of any one of meat, sausage, bread, chocolate, candy, snack, confectionery, pizza, ramen, gum, ice cream, soup, beverage, tea, functional water, drink, alcohol and vitamin complex.

In addition, the health functional food composition may further include a food additive and it suitability as a food additive is determined by the standards for the applicable item in accordance with General Regulations and General Test Methods of Korean Food Additives Codex approved by the Ministry of Food and Drug Safety, unless otherwise provided.

Examples of the items published in the above-mentioned Korean Food Additives Codex include chemical synthetics such as ketones, glycine, potassium citrate, nicotinic acid, and cinnamic acid and the like, natural additives such as persimmon extract, licorice extract, crystalline cellulose, kaoliang color and guar gum and the like, mixed preparations such as L-sodiumglutamate preparation, alkaline agents for noodles, preservative formulation and a tar color formulation and the like.

Moreover, the present invention provides a method of preparing a hydrogel formulation for delivering probiotics comprising: (1) preparing a mixed solution by adding probiotics and zwitterionic buffer to hydrogel solution; and (2) encapsulating the probiotics and the zwitterionic buffer in the hydrogel by dropping the mixed solution into a solution of calcium chloride ($CaCl_2$).

Namely, the method for preparing a hydrogel formulation for delivering probiotics according to the present invention uses a simple principle of gelation after mixing of each component without using other organic solvents and thus it is possible to efficiently prepare hydrogel formulations for delivering the probiotics.

At this time, in the step of (2), it may further comprise the step of freeze-drying the formulation, even though it undergoes this process, it is excellent in acid resistance activity and thus can effectively deliver probiotics to the intestine.

In detail, the hydrogel may be selected from the group consisting of alginate, pectin, carrageenan and gelatin, but it is not limited thereto.

The probiotics may be at least one selected from the group consisting of strains of *Lactobacillus* sp., *Streptococcus* sp., *Lactococcus* sp., *Enterococcus* sp., *Pediococcus* sp., *Leuconostock* sp., *Weissella* sp. and *Bifidobacterium* sp., but it is not limited thereto.

In more detail, the probiotics may be at least one selected from the group consisting of *Lactobacillus acidophilus, Lactobacillus casei, Lactobacilus gasseri, Lactobacillus delbrueckii* spp. *bulgaricus, Lactobacillus helveticus, Lactobacillus fermentum, Lactobacillus paracasei, Lactobacillus plantarum, Lactobacillus reuteri, Lactobacillus rhamnosus, Lactobacillus salivarius, Lactococcus lactis, Enterrococcus faecium, Enterococcus faecalis, Streptococcus thermophilus, Bifidobacterium bifidum, Bifidobacterium breve, Bifidobacterium longum* and *Bifidobacterium animalis* ssp. *lactis*, but it is not limited thereto.

The zwitterionic buffers may be selected from the group consisting of N-(2-hydroxyethyl)-piperazine-1-N'-2-ethanesulfonic acid (HEPES), glycine and betaine and thus in particular, the zwitterionic buffer has an excellent acid resistance improving effect and is preferable.

The weight ratio of the hydrogel and zwitterionic buffer may be 1:5 to 5:1, and particularly, the weight ratio of the hydrogel and zwitterionic buffer may be 1:5 to 1:1, and more particularly, the weight ratio of the hydrogel and the zwitterionic buffer may be 1:5, and when included in the above ratio, it is preferable because the delivery rate of the probiotics to the intestine is maximized, wherein the probiotics of 7 to 12 log CFU/g may be included.

In addition, in the hydrogel formulation, alginate is present in the form that alginate catches water, zwitterionic buffers and probiotics and thus it may further contain 80 parts by weight to 99.5 parts by weight of water relative to 100 parts by weight of the hydrogel formulation. However, the weight of water may be converged to zero by drying.

In one embodiment of the present invention, the formulation may further comprise carboxymethylcellulose, and in particular, it includes glycine as a zwitterionic buffer which is preferred because it can maximize the pH neutralizing effect.

In one embodiment of the present invention, the formulation may be in a regular form or an amorphous form having an average diameter of 200 to 3000 um, and may be in the form of a gel including water, but it is not limited thereto.

In addition, during the drying process, it may be in may be in a regular form or an amorphous form having an average diameter of 40 to 700 um, but it is not limited thereto.

More specifically, the hydrogel formulation may be, for example, in the form of beads, but it is not limited thereto.

Hereinafter, the present invention will be described in detail with reference to the following examples. The examples are only for describing the present invention in more detail and it is obvious to those skilled in the art that that the scope of the present invention is not limited by these examples embodiments in accordance with the gist of the present invention.

<Example 1> Preparation of Hydrogel-Based Composition for Delivering Probiotics

Firstly, alginate was used as a hydrogel, and *Lactobacillus rhamnosus* GG (KCTC, 5033) was used as probiotics. The strain was incubated for 24 to 48 hours in a shaking incubator (37° C., 220 rpm) and recovered, and the *Lactobacillus* strain and zwitterionic buffer HEPES were added to the alginate solution (1-3%) to make the weight ratio of the zwitterionic buffer and the alginate of 1:5 to 5:1. Thereafter the mixed alginate solution was placed in a syringe and dropped dropwise into a beaker containing $CaCl_2$ (0.05-0.50M) solution to prepare a bead-type hydrogel formulation with all probiotics and zwitterionic buffer and confirm by using SEM.

As a result, as shown in FIG. 3, it was confirmed that the *Lactobacillus* strain (above figure) was encapsulated inside the hydrogel (figure below).

Thereafter, only the *Lactobacillus* strain was encapsulated inside the hydrogel formulation without adding zwitterionic buffer solution, as a control to be used in the experiment.

<Example 2> Confirmation of Acid Resistance Effect of Hydrogel Formulation in Artificial Gastric Juice The hydrogel formulation containing the zwitterionic buffer of Example 1 and a control hydrogel formulation were prepared, but an indicator that changes color under acidic conditions was added to the mixed solution and it was added the formulation. Then, it was placed in artificial gastric juice having a pH of 2 and observed after 10 minutes.

As a result, as shown in FIG. 4, it was confirmed that the hydrogel containing the zwitterionic buffer according to the present invention maintained the internal pH of 3 or more, while the control formulation did not.

<Example 3> Confirmation of Acid Resistance Effect when Using Various Zwitterionic Buffers Hydrogel formulations were prepared according to the method described in the Example 1, except that glycine (Gly) and betaine were used instead of HEPES as a zwitterionic buffer. Because glycine can be used in foods, while HEPES is difficult to use, betaine which is similar in structure to glycine and can be used in foods, was used. At this time, the concentration and combination of each component were as shown in Table 1 below.

TABLE 1

| (mg/mL) | Positive control | Negative control | Alg + Glycine (15:75) | Alg + Betaine (15:75) | Alg + HEPES (15:75) |
|---|---|---|---|---|---|
| Alg | 15 | 15 | 15 | 15 | 15 |
| Gly | – | – | 75 | – | – |
| Betaine | – | – | – | 75 | – |
| HEPES | – | – | – | – | 75 |
| pH 2 (2 h) | – | + | + | + | + |

Then, the survival rates of *Lactobacillus* after 2 hours in artificial gastric juice of pH 2 of the hydrogel preparation and the control were measured. Specifically, after diluting serially from $10^0$ to $10^7$ in 0.1% peptone, plate counting using MRS agar was performed to measure the survival rate (CFU: colony forming unit), which was converted into log CFU/g and shown in the results. At this time, the experiment was conducted twice.

As a result, as shown in FIG. 5, when the probiotics were encapsulated in the alginate containing glycine (Alg+Glycine, 15:75), encapsulated in the alginate containing betaine (Alg+Betaine, 15:75), and encapsulated in the alginate containing HEPES (Alg+HEPES, 15:75), it was confirmed that all the cases significantly improved the acid resistance.

On the other hand, when glycine was included in the formulation, there was a slight variation in the survival rate test and thus, in the following experiment, carboxymethyl cellulose (CMC) was further added to alginate to maximize the effect of glycine.

<Example 4> Confirmation of Acid Resistance Effect According to Content of Zwitterionic Buffer In order to confirm whether the acid resistance changes according to the content of the zwitterionic buffer, the formulations were prepared as the added amount of glycine and HEPES to be mixed with alginate was adjusted to 0 to 300 mg/mL and the acid resistance effect was confirmed by the method performed in the Example 3. At this time, the content of each zwitterionic buffer was as shown in Table 2 below.

TABLE 2

| (mg/mL) | Positive Control | Negative Control | Alg + Glycine (15:15) | Alg + Glycine (15:75) | Alg + HEPES (15:15) | Alg + HEPES (15:75) |
| --- | --- | --- | --- | --- | --- | --- |
| Alg | 15 | 15 | 15 | 15 | 15 | 15 |
| Gly | – | – | 15 | 75 | – | – |
| HEPES | – | – | – | – | 15 | 75 |
| pH 2 (2 h) | – | + | + | + | + | + |

As a result, as shown in FIG. 6, the effect was best when 15 mg of alginate and 75 mg of zwitterionic buffer per 1 mL of water were contained, and when the zwitterionic buffer was included in the amount below or above the range, the problem of poor protection for probiotics at low pH occurred (not shown), and thus the optimum content was confirmed.

<Example 5> Confirmation of Acid Resistance Effect According to Amino Acid Type

In order to confirm whether acid resistance changes depending on the type of amino acid corresponding to the zwitterionic buffer, various amino acids were mixed in a slurry containing alginate and carboxymethyl cellulose, respectively, and gelated using calcium ions. The acid resistance effect for the prepared formulation was confirmed by the method performed in the Example 3. At this time, the type and content of each amino acid were shown in Table 3.

TABLE 3

| (mg/mL) | Alg | Alg + CMC | Alg + CMC + Glycine | Alg + CMC + Glutamine | Alg + CMC + Histidine | Alg + CMC + Serine | Alg + CMC + Protine |
| --- | --- | --- | --- | --- | --- | --- | --- |
| Alginate | 15 | 15 | 15 | 15 | 15 | 15 | 15 |
| CMC | – | 5 | 5 | 5 | 5 | 5 | 5 |
| Gly | – | – | 50 | – | – | – | – |
| Glu | – | – | – | 50 | – | – | – |
| His | – | – | – | – | 50 | – | – |
| Ser | – | – | – | – | – | 50 | – |
| Pro | – | – | – | – | – | – | 50 |
| pH 2 (2 h) | + | + | + | + | + | + | + |

As a result, as shown in FIG. 7, the acid resistance effect of the formulation containing glycine was particularly excellent compared to other amino acids. On the other hand, proline did not show any acid resistance effect and it was confirmed that only glycine is the most optimized amino acid for the formulation for delivering the probiotics.

<Example 6> Confirmation of Acid Resistance Effect According to Freeze-Drying

In order to commercialize the formulation, it must be subjected to a freeze-drying process. In order to confirm whether the freeze-drying of the formulation changes in acid resistance, glycine was mixed in a slurry containing alginate and carboxymethyl cellulose, gelated using calcium ions and the formulation thus prepared was freeze-dried. Then, the acid resistance effect was confirmed by the method performed in the Example 3. At this time, the components of each formulation were shown in Table 4.

TABLE 4

| (mg/mL) | Positive control | Negative Control | Alg (15) | Alg + CMC (15:5) | Alg + CMC + Glycine (15:5:75) |
| --- | --- | --- | --- | --- | --- |
| Alg | 15 | 15 | 15 | 15 | 15 |
| CMC | – | – | – | 5 | 5 |
| Gly | – | – | – | – | 75 |
| Trehalose | + | + | + | + | + |
| Freeze-drying | + | + | + | + | + |
| pH 2 (2 h) | – | + | + | + | + |

As a result, as shown in FIG. 8, even after the freeze-drying, the gel formulation containing alginate, carboxymethyl cellulose and glycine was confirmed that the acid resistance effect for probiotics is excellent.

<Example 7> Comparison of Acid Resistance Effect with Commercialized Products

To compare the acid resistance effects of current commercially available probiotics products (G products (#A) of Company I and D products (#B) of Company C) and formulations comprising alginate and HEPES according to the invention, the products were stored in the refrigerator after purchase from the company's web page, and the experiment was conducted two months before receipt. Specifically, the formulation was prepared according to the method disclosed in the Example 1 by mixing the components in the content shown in Table 5 below, and the acid resistance effect was confirmed as described in the Example 3 together with #A and #B.

TABLE 5

| (mg/mL)   | #A  | #B  | Alg + HEPES (15:75) |
|-----------|-----|-----|---------------------|
| Sample    | A   | B   | C                   |
| Alg       | –   | –   | 15                  |
| HEPES     | –   | –   | 75                  |
| pH 2 (2 h)| +/– | +/– | +/–                 |

As a result, as shown in FIG. 9, it was confirmed that the formulation according to the present invention exhibited a significant acid resistance effect than #A and #B in the environment of pH 2.

While the present invention has been particularly described with reference to specific embodiments thereof, it is apparent that this specific description is only a preferred embodiment and that the scope of the present invention is not limited thereby to those skilled in the art. That is, the practical scope of the present invention is defined by the appended claims and their equivalents.

The invention claimed is:

1. A probiotics-delivering hydrogel formulation for protecting probiotics in acidic environment, consisting of:
   a hydrogel;
   probiotics; and
   zwitterionic buffer,
   wherein the probiotics are encapsulated in a composition consisting of 15 mg of hydrogel and 75 mg of zwitterionic buffer per 1 mL of water,
   wherein the hydrogel consists of alginate and carboxymethylcellulose,
   wherein the zwitterionic buffer is N-(2-hydroxyethyl)-piperazine-l-N'-2-ethanesulfonic acid (HEPES),
   wherein the zwitterionic buffer improves acid resistance of the probiotics-delivering hydrogel formulation by neutralizing hydrogen ions entering the probiotics-delivering hydrogel formulation to deliver probiotics to intestine.

2. The probiotics-delivering hydrogel formulation of claim 1, wherein the probiotics are at least one selected from the group consisting of strains of *Lactobacillus* sp., *Streptococcus* sp., *Lactococcus* sp., *Enterococcus* sp., *Pediococcus* sp., Leuconostock sp., Weissella sp. and *Bifidobacterium* sp.

3. The probiotics-delivering hydrogel formulation of claim 1, wherein the formulation is freeze-dried.

4. A pharmaceutical composition for protecting probiotics in acidic environment comprising the hydrogel formulation of claim 1 as an active ingredient.

5. A health functional food composition for protecting probiotics in acidic environment comprising the hydrogel formulation of claim 1 as an active ingredient.

* * * * *